US010952655B1

(12) United States Patent
Jiao et al.

(10) Patent No.: US 10,952,655 B1
(45) Date of Patent: Mar. 23, 2021

(54) RETINAL BLOOD VESSEL OXIMETRY USING RETINAL AUOFLUORESCENCE

(71) Applicants: Shuliang Jiao, Miami, FL (US); Rong Wen, Coral Gables, FL (US); Chuanqing Zhou, Coral Gables, FL (US)

(72) Inventors: Shuliang Jiao, Miami, FL (US); Rong Wen, Coral Gables, FL (US); Chuanqing Zhou, Coral Gables, FL (US)

(73) Assignees: The Florida International University Board of Trustees, Miami, FL (US); University of Miami, Miami, FL (US)

( * ) Notice: Subject to any disclaimer, the term of this patent is extended or adjusted under 35 U.S.C. 154(b) by 0 days.

(21) Appl. No.: 17/026,415

(22) Filed: Sep. 21, 2020

(51) Int. Cl.
*A61B 5/1455* (2006.01)
*A61B 5/00* (2006.01)

(52) U.S. Cl.
CPC ........ *A61B 5/14555* (2013.01); *A61B 5/0059* (2013.01); *A61B 5/7271* (2013.01)

(58) Field of Classification Search
CPC .............. A61B 5/1455; A61B 5/14555; A61B 5/14556; A61B 5/72; A61B 5/7271
See application file for complete search history.

(56) References Cited

U.S. PATENT DOCUMENTS

| | | | | | |
|---|---|---|---|---|---|
| 6,161,028 | A | * | 12/2000 | Braig | A61B 5/0059 600/310 |
| 6,276,798 | B1 | * | 8/2001 | Gil | A61B 5/0059 351/206 |
| 6,697,657 | B1 | * | 2/2004 | Shehada | A61B 5/0075 600/317 |
| 6,728,561 | B2 | * | 4/2004 | Smith | A61B 5/14555 600/323 |
| 2004/0156016 | A1 | * | 8/2004 | Kerr | A61B 5/14555 351/206 |
| 2008/0273172 | A1 | * | 11/2008 | Spaide | A61B 3/1233 351/206 |

* cited by examiner

*Primary Examiner* — Eric F Winakur
(74) *Attorney, Agent, or Firm* — Saliwanchik, Lloyd & Eisenschenk

(57) ABSTRACT

Systems and methods for quantitatively imaging retinal blood vessel oxygen saturation using retinal auto-fluorescence (AF) are provided. One or more excitation sources can be used to provide light to the retina, and retinal AF can be detected by one or more detectors. The quantitative level of oxygen saturation in the blood can be determined based on the intensity of AF.

20 Claims, 6 Drawing Sheets

RETINAL BLOOD VESSEL OXIMETRY USING RETINAL AUOFLUORESCENCE

BACKGROUND

Oxygen supply to retinal neurons is vital to their survival and functions. Reduced oxygen supply leads to hypoxia in the retina, which can have pathological consequences, including retinal edema (especially in the macular region), neovascularization, and even cell death. This is seen in many retinal diseases, including diabetic retinopathy, age-related macular degeneration, glaucoma, and retinopathy of prematurity. Assessing the oxygen saturation in the retinal vasculature is therefore of great clinical value.

BRIEF SUMMARY

Embodiments of the subject invention provide novel and advantageous systems and methods for quantitatively determining and/or imaging retinal blood vessel oxygen saturation ($SO_2$) using retinal auto-fluorescence (AF). One or more excitation sources (e.g., lasers) can be used to provide light to the retina (e.g., to the retinal pigment epithelium), and retinal AF can be detected by one or more detectors. The quantitative level of $SO_2$ in the blood can be determined based on the intensity of AF. If multiple excitation sources are present, they can provide light at different wavelengths from each other, though embodiments are not limited thereto. If multiple detectors are present, they can be configured to detect different wavelengths from each other, though embodiments are not limited thereto. The one or more detectors can be in operable communication with a processor and/or machine-readable medium (e.g., with a device having a processor and/or machine-readable medium, such as computer or similar device); the output of the one or more detectors can be digitized and analyzed by the processor or device having a processor to determine the $SO_2$ based on the detected AF. In certain cases where multiple excitation wavelengths are used, the acquired retinal image can be filtered at each modulation frequency to get the AF image of each excitation wavelength. The systems and methods described herein improve the accuracy of retinal oxygen saturation measurements by overcoming difficulties and challenges in the art and avoiding deficiencies of related art devices used for retinal oximetry.

In an embodiment, a system for quantitatively determining retinal blood vessel oxygen saturation can comprise: at least one excitation source (e.g., at least two excitation sources) configured to provide light to a retina; at least one detector configured to detect AF light from the retina; and a device in operable communication with the at least one detector and having a processor and a machine-readable medium, the machine-readable medium having instructions stored thereon that, when executed by the processor, determine the retinal blood vessel oxygen saturation of the retina based on AF of the light detected by the at least one detector. The at least one excitation source can include a laser, and the at least one excitation source can provide light at a wavelength in a range of from 450 nanometers (nm) to 520 nm. The system can be configured such that the light from the at least one excitation source is provided to retinal pigment epithelium (RPE) of the retina.

In another embodiment, a method for quantitatively determining retinal blood vessel oxygen saturation can comprise: providing light to a retina using at least one excitation source (e.g., at least two excitation sources); detecting AF light from the retina using at least one detector (e.g., at least two detectors); and determining, using a processor, the retinal blood vessel oxygen saturation of the retina based on AF of the light detected by the at least one detector. The at least one excitation source can be a laser, and the at least one excitation source can provide light at a wavelength in a range of from 450 nm to 520 nm. The light from the at least one excitation source can be provided to RPE of the retina.

BRIEF DESCRIPTION OF THE DRAWINGS

In FIG. 1: FC1 is a first fiber coupler; FC2 is a second fiber coupler; FC3 is a third fiber coupler; PD is a photodiode; PMT is a photo multiplier tube; PH is a pin hole; LPF is a long-pass filter; DM1 is a first dichroic mirror; DM2 is a second dichroic mirror; GM is a galvanometer; L1 is a first lens; L2 is a second lens; PC is a polarization controller; SLD is a super-luminescent diode; SPEC is a spectrometer; CCD is a charge coupled device (CCD) or complementary metal oxide semiconductor (CMOS) line scan camera; G2 is a glass plate; FP4 is a first fiber port; FP5 is a second fiber port; FP6 is a third fiber port; M2 is a mirror; G2 is a glass plate; IRIS2 is an iris; and ISO is an isolator.

In FIG. 2: FC3 is a fiber coupler; PMT is a photo multiplier tube; PH is a pin hole; BPF is a band-pass filter; DM1 is a first dichroic mirror; DM2 is a second dichroic mirror; GM is a galvanometer; L1 is a first lens; L2 is a second lens; PC is a polarization controller; SLD is a super-luminescent diode; SPEC is a spectrometer; CCD is a CCD or CMOS line scan camera; G2 is a glass plate; FP4 is a first fiber port; FP5 is a second fiber port; FP6 is a third fiber port; M2 is a mirror; G2 is a glass plate; IRIS2 is an iris; and ISO is an isolator.

DETAILED DESCRIPTION

Figure 1:
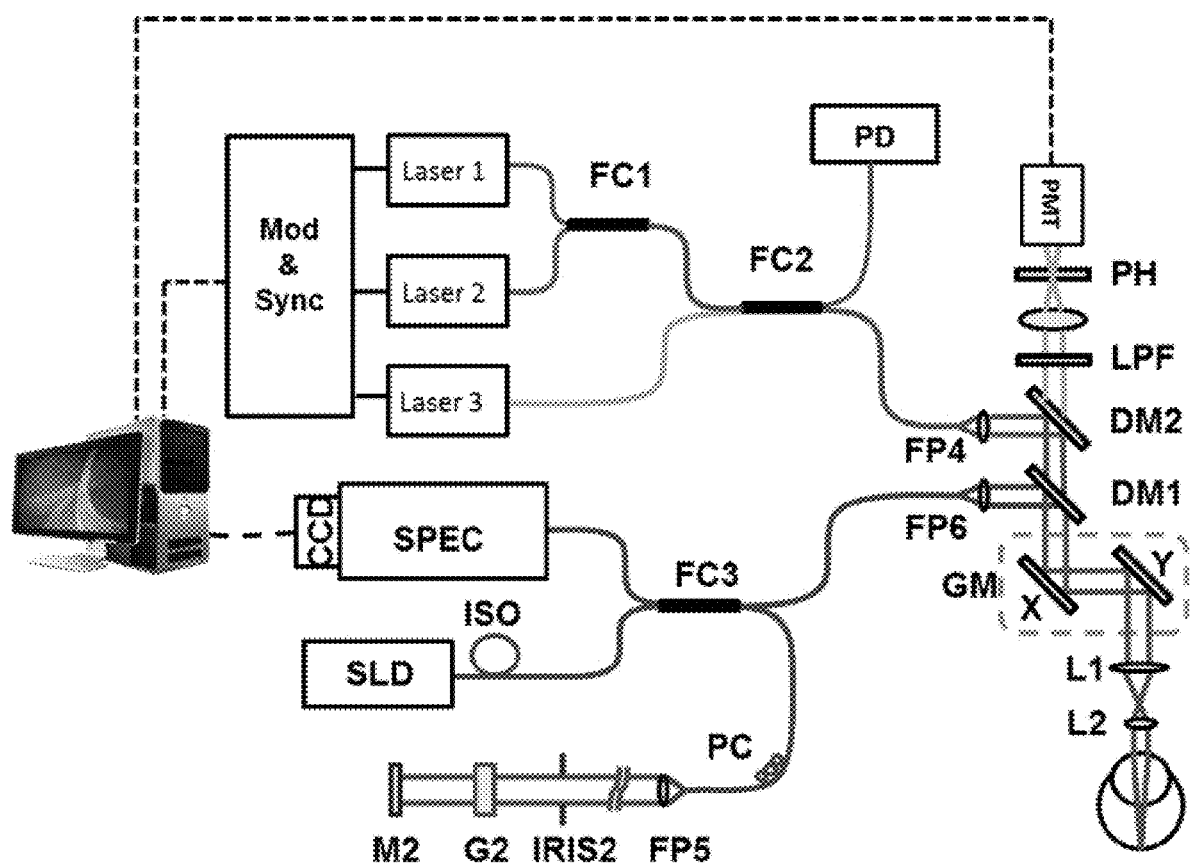
FIG. 1 shows a schematic view of a system for retinal blood vessel oximetry, according to an embodiment of the subject invention.

Embodiments of the subject invention provide novel and advantageous systems and methods for quantitatively determining and/or imaging retinal blood vessel oxygen saturation ($SO_2$) using retinal auto-fluorescence (AF). One or more excitation sources (e.g., lasers) can be used to provide light to the retina (e.g., to the retinal pigment epithelium), and retinal AF can be detected by one or more detectors. The quantitative level of $SO_2$ in the blood can be determined based on the intensity of AF. If multiple excitation sources are present, they can provide light at different wavelengths from each other, though embodiments are not limited thereto. If multiple detectors are present, they can be configured to detect different wavelengths of the AF from each other, though embodiments are not limited thereto. The one or more detectors can be in operable communication with a processor and/or machine-readable medium (e.g., with a device having a processor and/or machine-readable medium, such as computer or similar device); the output of the one or more detectors can be digitized and analyzed by the processor or device having a processor to determine the $SO_2$ based on the detected AF. In certain cases where multiple wavelengths are used for excitation, the acquired retinal image can be filtered at each modulation frequency of the light source to get the image of each excitation wavelength. The systems and methods described herein improve the accuracy of retinal oxygen saturation measurements by overcoming difficulties and challenges in the art and avoiding deficiencies of related art devices used for retinal oximetry.

Hemoglobin in red blood cells receives oxygen in the lungs and transports it to other tissues in the body. Oxygen saturation is the fraction of oxygenated (or oxygen saturated) hemoglobin in the blood relative to the total hemoglobin (unsaturated+saturated, or deoxygenated+oxygenated). That is, oxygen saturation is oxygenated hemoglobin (HbO) divided by total hemoglobin (HbO/(HbO+Hb), where Hb is deoxygenated hemoglobin). The oxygenated (HbO) and deoxygenated hemoglobin (Hb) have distinguished absorption spectra, so the fractions of light absorption by HbO and Hb are determined by their molar extinction coefficients and concentrations in the blood. Thus, when light of a given wavelength passes through the blood vessels, it is partially absorbed by the hemoglobin. Oxygen saturation can then be calculated by hemoglobin absorption, and this is a basic concept of oximetry.

Unlike in other tissues in which oxygen saturation is measured by passing a light beam through the tissue and detecting it on the other side, related art retinal oximetry measures the reflection of the incident light that passes through a blood vessel. This makes retinal oximetry difficult because light detected could come from several sources even though it may seem to be from the location of a retinal blood vessel. For example, one fraction of light could come from the reflection of the first surface of the blood vessel the light encounters. This fraction of light would not pass through the blood stream and therefore would not be absorbed by hemoglobin, meaning that it would carry no information related to oxygen saturation. Another fraction could come from the surface of the blood vessel on the other side of the blood stream. It would then be absorbed by the same volume of blood twice as it passes through the blood stream forth and back. In addition, light reflected from tissues other than the blood vessel could contaminate the measurement. The multiple sources of detected light make it difficult to accurately calculate the real oxygen saturation in retinal blood vessels using related art retinal oximetry techniques.

Embodiments of the subject invention overcome the deficiencies of the related art devices and techniques to accurately image retinal blood vessel saturation quantitatively. Instead of measuring the reflection of incident light, signals carried by the retinal auto-fluorescence (AF) are used to calculate oxygen saturation. This technique uses incident light within the excitation spectrum of lipofuscin (i.e., within a range of from 450 nanometers (nm) to 520 nm) to generate AF (for example, AF in the retinal pigment epithelium (RPE)) and detect the intensity of AF. When the light passes through a retinal blood vessel, it is absorbed by HbO and Hb before reaching the RPE. The absorption weakens the light and, as a result, weaker AF is generated. The decrease in AF is proportional to the amount of incident light absorption by HbO and Hb in blood, so the quantitative level of oxygen saturation in the blood can be determined based on the intensity of AF. The incident light can be a single-wavelength or multiple-wavelength (e.g., dual-wavelength, three wavelengths, or more) configuration. Depending on the incident light configuration used, an appropriate algorithm can be used to calculate the oxygen saturation based on the AF generated and/or detected.

FIG. 1 shows a schematic view of a system for retinal blood vessel oximetry, according to an embodiment of the subject invention. Referring to FIG. 1, three excitation sources (e.g., lasers) can be modulated and coupled into the same single-mode optical fiber coupler. Each excitation source can have a different modulation frequency from the other lasers, or some or all of the lasers can have the same frequency separated in a time sequence. The three modulated excitation light beams can reach each scanning point on the retina either simultaneously or sequentially. At each scanning point the output of one or more detectors (e.g., one detector that can be, for example, a photomultiplier tube (PMT)) can be digitized and recorded for a predetermined period of time, which can be set based on the scanning rate (e.g., 36 microseconds (s) when the scanning rate is 24,000 points per second). The acquired retinal image can be filtered at each modulation frequency to get the image of each excitation wavelength. Although FIG. 1 depicts the excitation sources as lasers and the detector as a PMT, these are for exemplary purposes only and should not be construed as limiting; other excitation sources and/or detector(s) can be used.

In a configuration using three wavelengths of incident light and a single detector, the incident light intensity can be expressed as $I_0(\lambda_i)$, where $\lambda_i$ is the wavelength of the incident light. After passing through a blood vessel the light intensity is $I_1(\lambda_i)$. Outside blood vessels, the lipofuscin AF signal intensity can be expressed as $$I_{AF} = I_0(\lambda_i) \sum_\lambda S_{lipo}(\lambda, \lambda_i),$$

where $S_{lipo}(\lambda,\lambda_i)$ is the power density of the AF signal at AF wavelength $\lambda$, which can be expressed as $$S_{lipo}(\lambda,\lambda_i) = \varepsilon_{lipo}(\lambda_i) C_{lipo} \eta_{lipo}(\lambda) d_{RPE},$$

$\varepsilon_{lipo}(\lambda_i)$: molar extinction coefficient of lipofuscin at the incident wavelength;

$C_{lipo}$: molar concentration of lipofuscin in the RPE;

$\eta_{lipo}(\lambda)$: quantum yield of lipofuscin AF at wavelength $\lambda$; and $d_{RPE}$: the thickness of the RPE layer.

At the location of a blood vessel, the AF signal intensity is $$I_{AFV} = I_1(\lambda_i) \sum_\lambda S_{lipo}(\lambda, \lambda_i) 10^{-\varepsilon(\lambda)Cd},$$

where $\varepsilon(\lambda)$ is the molar extinction coefficient of hemoglobin at AF wavelength $\lambda$, C is the concentration of hemoglobin, and d is the vessel diameter. The ratio of the AF intensity in ($I_{AFV}$) and outside ($I_{AF}$) of the blood vessel can be expressed as $$\frac{I_{AFV}}{I_{AF}} = \frac{I_1(\lambda_i)}{I_0(\lambda_i)} \cdot \frac{\sum_\lambda S_{lipo}(\lambda, \lambda_i) 10^{-\varepsilon(\lambda)Cd}}{\sum_\lambda S_{lipo}(\lambda, \lambda_i)}$$

$$= \frac{I_1(\lambda_i)}{I_0(\lambda_i)} \cdot \sum_\lambda \frac{S_{lipo}(\lambda, \lambda_i) 10^{-\varepsilon(\lambda)Cd}}{\sum_\lambda S_{lipo}(\lambda, \lambda_i)}$$

$$= \frac{I_1(\lambda_i)}{I_0(\lambda_i)} \cdot \sum_\lambda G(\lambda, \lambda_i) 10^{-\varepsilon(\lambda)Cd},$$

where $G(\lambda,\lambda_i)$ is power density of AF spectrum at the incident wavelength $\lambda_i$. The optical density of a blood vessel (OD) can be expressed as $$OD = [\varepsilon_{Hb} + (\varepsilon_{HbO} - \varepsilon_{Hb})O_{2sat}] \cdot C \cdot d$$

where $\varepsilon_{Hb}$ and $\varepsilon_{HbO}$ are the molar extinction coefficients of the deoxygenated hemoglobin (Hb) and oxygenated hemoglobin (HbO), respectively. OD of the detected AF signal for a blood vessel is $$OD_{AFV} = -\log\left(\frac{I_{AFV}}{I_{AF}}\right)$$

$$= -\log\left[\frac{I_1(\lambda_i)}{I_0(\lambda_i)}\right] - \log\left[\sum_\lambda G(\lambda, \lambda_i) 10^{-\varepsilon(\lambda)Cd}\right]$$

$$= OD_i + OD_{AF}$$

When three excitation wavelengths are used, $$OD_{AFV}(\lambda_i) = OD_i(\lambda_i) + OD_{AF}(\lambda_i), i=1,2,3.$$

When the three incident wavelengths are close to each other, the AF spectra are identical and $$OD_{AF}(\lambda_1) = OD_{AF}(\lambda_2) = OD_{AF}(\lambda_3)$$

If $\lambda_1$ is an isosbestic wavelength (for example, $\lambda_1$=505 nm), then $\varepsilon_{Hb}(\lambda_1) = \varepsilon_{HbO}(\lambda_1) = \varepsilon_{ISO}(\lambda_1)$, and the oxygen saturation ($O_{2sat}$=HbO/(Hb+Hb)) can be calculated as $$O_{2sat} = \frac{\{[OD_{AFV}(\lambda_3) - OD_{AFV}(\lambda_1)]\varepsilon_{Hb}(\lambda_2) - [OD_{AFV}(\lambda_2) - OD_{AFV}(\lambda_1)]\varepsilon_{Hb}(\lambda_3) + [OD_{AFV}(\lambda_2) - OD_{AFV}(\lambda_3)]\varepsilon_{ISO}(\lambda_1)\}}{[OD_{AFV}(\lambda_2) - OD_{AFV}(\lambda_1)]\varepsilon_{HbO-Hb}(\lambda_3) - [OD_{AFV}(\lambda_3) - OD_{AFV}(\lambda_1)]\varepsilon_{HbO-Hb}(\lambda_2)},$$

where the following term is defined $$\varepsilon_{HbO-Hb}(\lambda_i) = \varepsilon_{HbO}(\lambda_i) - \varepsilon_{Hb}(\lambda_i).$$

In a configuration using two excitation sources with different wavelengths and a single detector (similar setup as in FIG. 1, but with just two excitation sources), the $O_{2sat}$ can be calculated as $$O_{2sat} = \frac{OD_{AFV}(\lambda_2) - OD_{AFV}(\lambda_1)}{\varepsilon_{HbO-Hb}(\lambda_2) \cdot C \cdot d} - \frac{\varepsilon_{Hb}(\lambda_2) - \varepsilon_{ISO}(\lambda_1)}{\varepsilon_{HbO}(\lambda_2) - \varepsilon_{Hb}(\lambda_2)}.$$

With this configuration the vessel diameter (d) and the concentration of hemoglobin (C) need to be measured.

Figure 2:
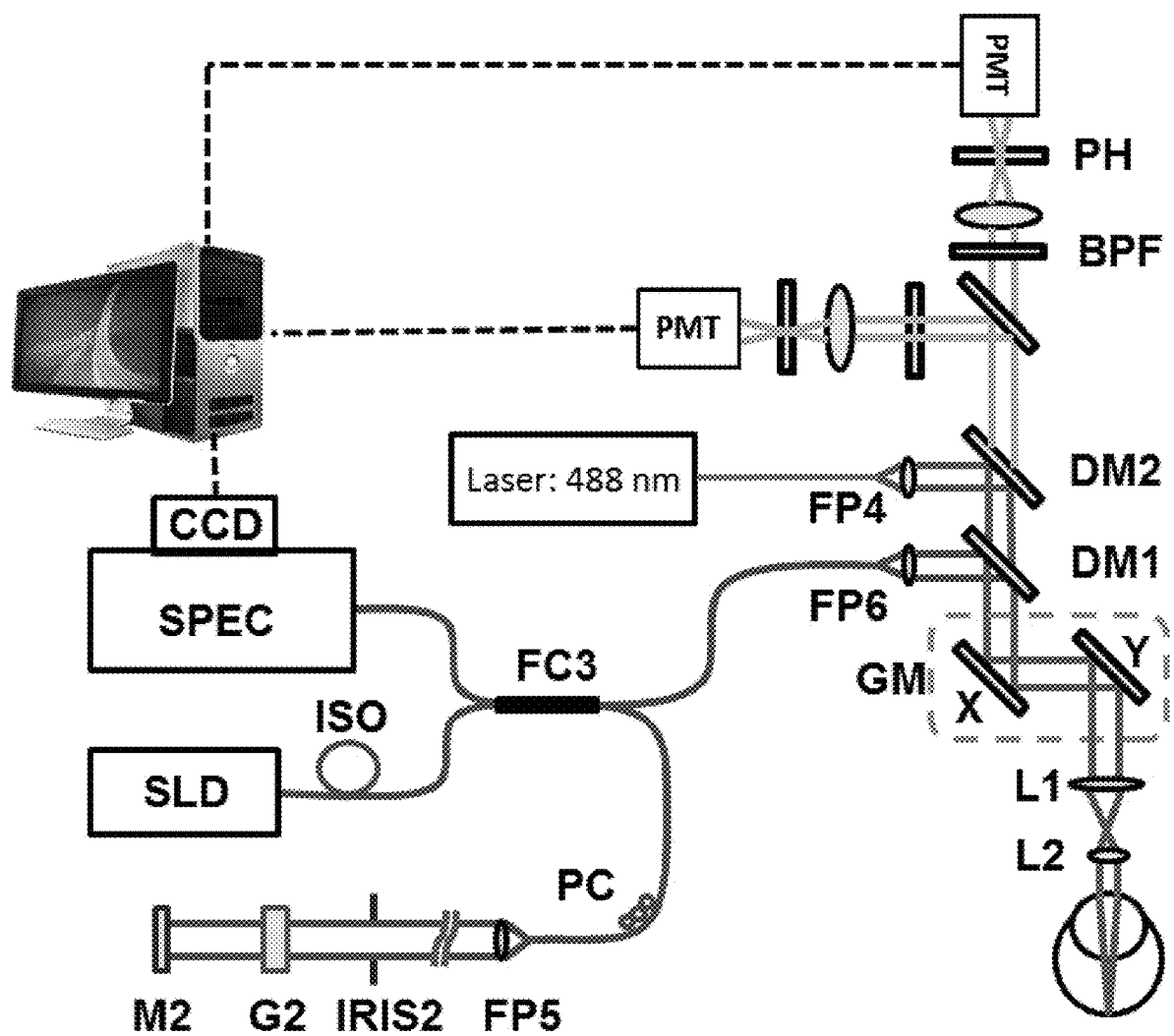
FIG. 2 shows a schematic view of a system for retinal blood vessel oximetry, according to an embodiment of the subject invention.

FIG. 2 shows a schematic view of a system for retinal blood vessel oximetry, according to an embodiment of the subject invention. Referring to FIG. 2, one excitation source (e.g., a laser) can be used, along with two detectors (e.g., PMTs). The excitation light beam can reach each scanning point on the retina and then be detected by the detector(s). At each scanning point the output of the one or more detectors can be digitized and recorded for a predetermined period of time, which can be set based on the scanning rate (e.g., 36 microseconds (µs) when the scanning rate is 24,000 points per second). The acquired retinal images can be filtered to get the overall image at the excitation wavelength. Although FIG. 2 depicts the excitation source as a laser, the detectors as PMTs, and the excitation wavelength as 488 nm, these are for exemplary purposes only and should not be construed as limiting; other excitation source(s), detector(s), and/or excitation wavelengths can be used.

In a configuration using only one excitation source, two detection channels can be used to detect two different wavelengths of the lipofuscin AF. For example, an isosbestic wavelength can be used for the incident light (for example, $\lambda_i$=505 nm). The molar extinction coefficient of hemoglobin at this wavelength is $\varepsilon_{ISOi}(\lambda_i)$. One of the two detection channels detects the AF signal at an isosbestic wavelength (for example, by selecting a filter $\lambda_1$=586 nm) while the other detection channel detects the AF signal at an oxygen sensitive wavelength (for example, $\lambda_2$=640 nm. The oxygen saturation can be calculated using the below.

$$O_{2sat} = \frac{OD_{AFV}(\lambda_2)(\varepsilon_{ISO} + \varepsilon_{ISOi}) - OD_{ISO}(\lambda_1)(\varepsilon_{Hb} + \varepsilon_{ISOi})}{\varepsilon_{HbO-Hb}(\lambda_2)OD_{ISO}(\lambda_1)}$$

where $\varepsilon_{ISO}$ is the isosbestic molar extinction coefficient at $\lambda_1$, $\varepsilon_{ISOi}$ is the isosbestic molar extinction coefficient at the excitation wavelength, and $OD_{ISO}(\lambda_1) = (\varepsilon_{ISO} + \varepsilon_{ISOi})Cd$.

Embodiments of the subject invention can be used in many settings including but not limited to ophthalmology clinics for diagnosis and follow-up of diseases associated with retinal metabolism abnormalities. Such diseases include but are not limited to diabetic retinopathy, age-related macular degeneration, glaucoma, retinopathy of prematurity, retinal artery occlusion, and retinal vein occlusion.

Embodiments of the subject invention have at least two major advantages over the related art retinal oximetry techniques. First, embodiments of the subject invention do not detect reflected incident light and therefore do not suffer from the technical issues that traditional retinal oximetry faces. Second, AF is mainly emitted by lipofuscin, from fluorogenic granules in RPE cells when excited by light having a wavelength in a range of from 450 nm to 520 nm. RPE cells are located at the back of the retina and thus at the back of all retinal blood vessels. The definite spatial relationship between the retinal vessels and the RPE where AF is generated makes it unlikely for light from other sources to contaminate the measurement. Thus, the embodiments of the subject invention are more reliable and more accurate for quantifying retinal blood oxygen saturation.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

Example 1

Figure 3:
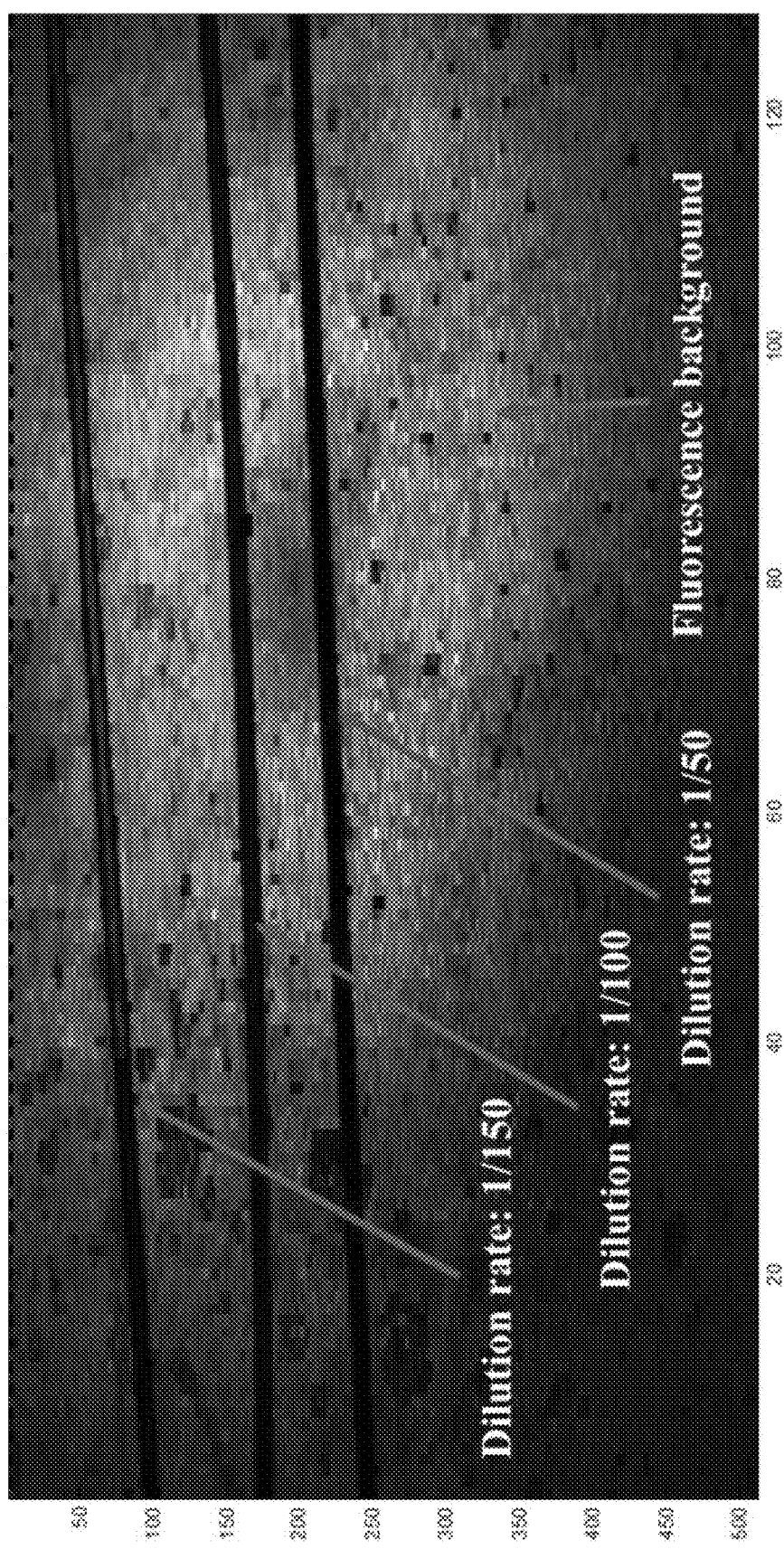
FIG. 3 shows en face imaging of a phantom.

An experiment was performed using phantom dye. To design the phantom dye, an original Red 40 dye solution was diluted to the relative concentrations of 1/50, 1/75, 1/100, and 1/150, respectively. Capillary tubes with inner diameter of 100 micrometer (μm), which was measured with an optical coherence tomography (OCT) scan, were filled with the diluted dye solutions. One piece of paper was immersed into fluorescein solution and dried. The tubes were the placed on the paper to mimic the vessels. FIG. 3 shows en face imaging of the phantom dye.

The phantom was scanned transversely with a system as described herein (see also, e.g., FIGS. 1 and 2). The light intensities from the center and outside of the tubes, which were labeled with $I_{in}$ and $I_{out}$ respectively, were acquired. Then measured optical density of a blood vessel ($OD_{measured}$) was determined with the following formula, $$OD(\lambda)_{measured} = -\log_{10} \frac{I_{in}(\lambda)}{I_{out}(\lambda)}$$

For comparison, the theoretical values of OD ($OD_{cal}$) were calculated as follows, $$OD(\lambda)_{cal} = -\log_{10}\frac{I(\lambda)}{I_0(\lambda)} = -\log_{10}(e^{-2\mu_\alpha(\lambda)d}) = -2\mu_\alpha(\lambda)d * \log_{10}e = -0.87\mu_\alpha(\lambda)d$$

where $\mu_\alpha(\lambda)$ is the extinction coefficient of the diluted dye solution for wavelength λ, which was measured with a spectroscope, and d is the internal diameter of the capillary tube.

Figure 4:
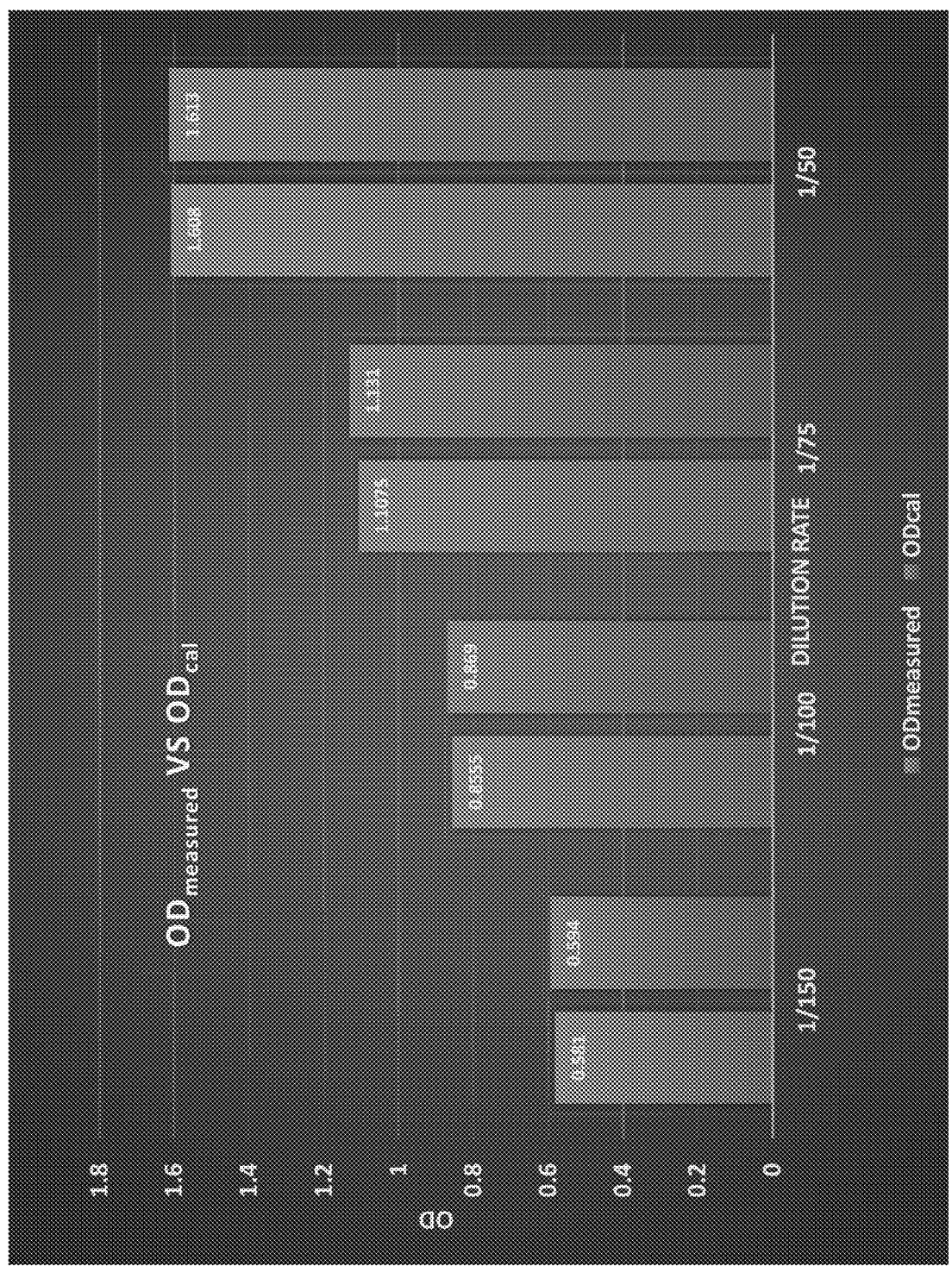
FIG. 4 shows a bar chart comparison of measured optical density of a blood vessel (OD) versus calculated OD.

The measured $OD_{measured}$ and calculated $OD_{cal}$ are shown as in FIG. 4. The highest error was only 2%, which was possibly due to the measuring error of extinction coefficients of the diluted fluorescein solution and/or fluoresce intensities.

Example 2

Figure 5:
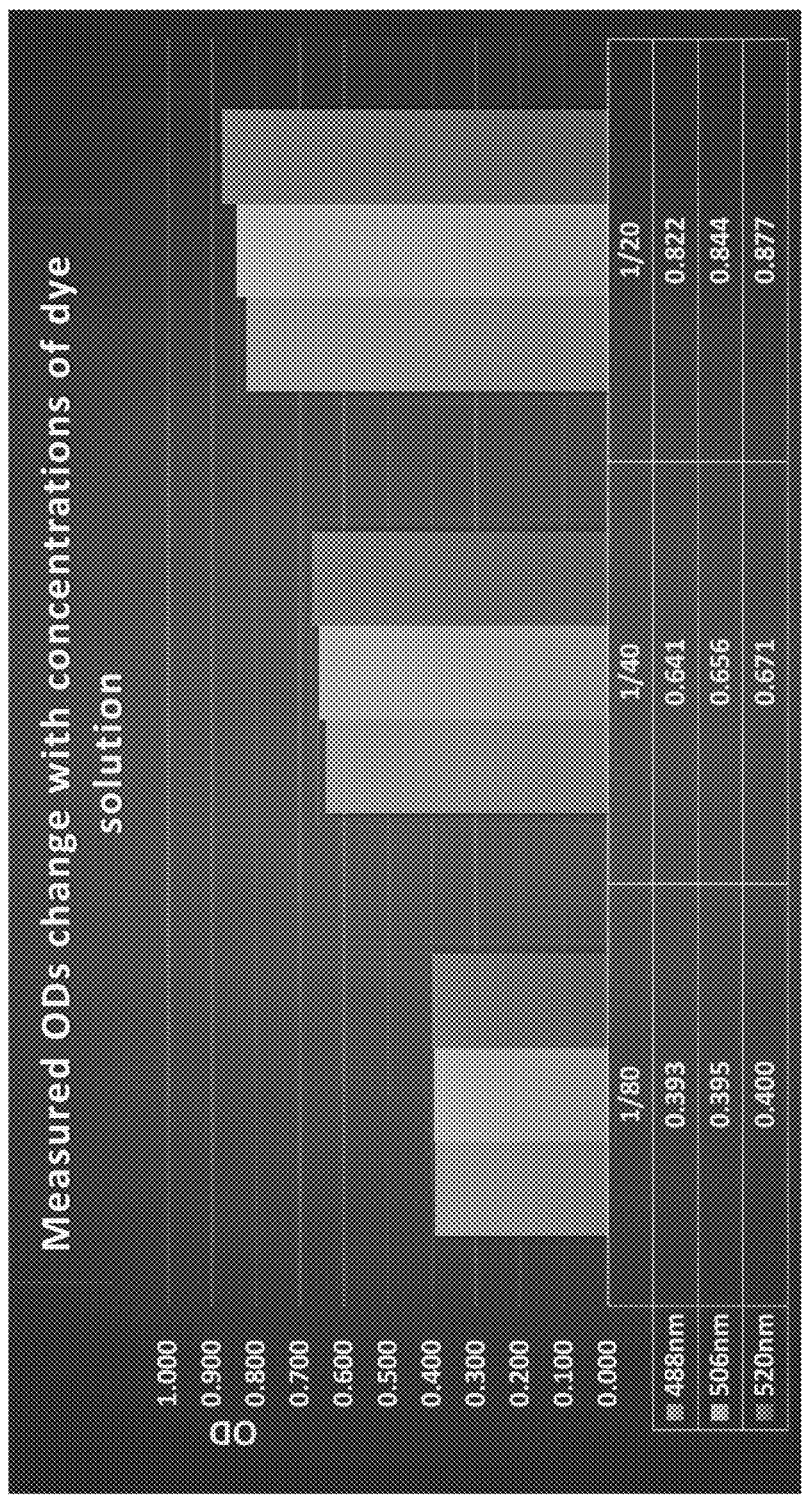
FIG. 5 shows a bar chart comparison of measured OD change at different relative concentrations of dye solution.

A multi-wavelength experiment was performed. Using Blue 1 solution, the experiment of Example 1 was repeated with three wavelengths of 488 nanometers (nm), 506 nm, and 520 nm. The original dye solution was diluted to the concentrations of 1/80, 1/40, and 1/20, respectively. The measured OD(λ) is shown in FIG. 5.

Figure 6:
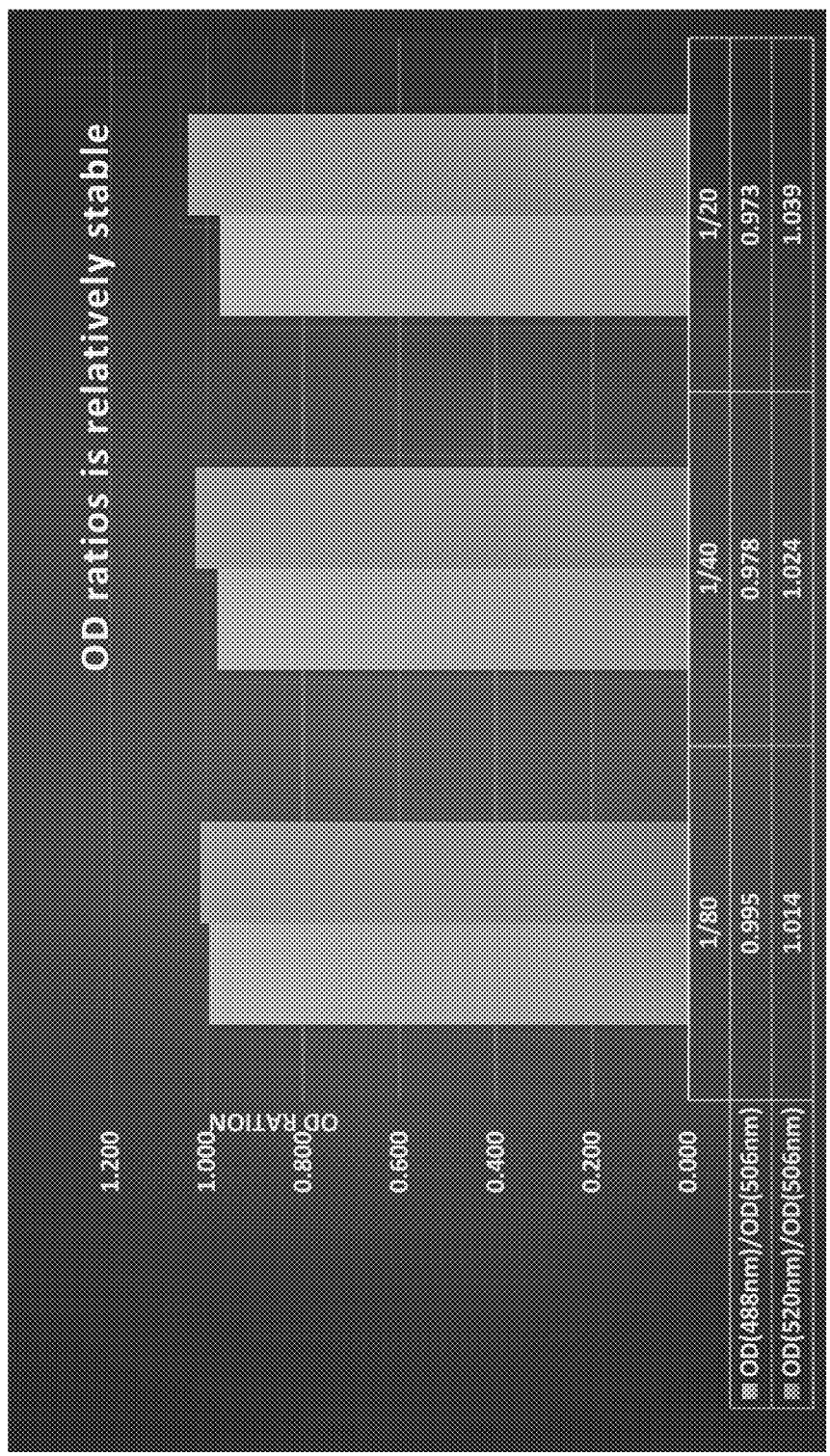
FIG. 6 shows a bar chart comparison showing OD ratios remaining relatively stable as concentration of dye solution changes.

Next, OD ratios were calculated for the three wavelengths ($OD_{(488\ nm)}/OD_{(506\ nm)}$ and $OD_{(520\ nm)}/OD_{(506\ nm)}$). It was found that the OD ratios kept relatively constant as shown in FIG. 6. The highest error of OD ratio was only 1%, which demonstrated excellent accuracy of the methods and systems described herein. The oxygen saturation ($SO_2$) is expected to have excellent accuracy because the oxygen saturation was determined with the OD ratios.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for quantitatively determining retinal blood vessel oxygen saturation, the system comprising:
    at least one excitation source configured to provide light to a retina;
    at least one detector configured to detect auto-fluorescence (AF) light generated from the retinal pigment epithelium (RPE) of the retina; and
    a device in operable communication with the at least one detector and having a processor and a machine-readable medium, the machine-readable medium having instructions stored thereon that, when executed by the processor, determine the retinal blood vessel oxygen saturation of the retina based on the AF light detected by the at least one detector.

2. The system according to claim 1, the at least one excitation source being a laser.

3. The system according to claim 1, the at least one excitation source providing light at a wavelength in a range of from 450 nanometers (nm) to 520 nm.

4. The system according to claim 1, the system being configured such that the light from the at least one excitation source is provided to the RPE of the retina.

5. The system according to claim 1, the at least one excitation source comprising a first excitation source providing light at a first wavelength ($\lambda_1$), a second excitation source providing light at a second wavelength ($\lambda_2$) different from $\lambda_1$, and a third excitation source providing light at a third wavelength ($\lambda_3$) different from $\lambda_1$ and $\lambda_2$.

6. The system according to claim 5, the determining of the retinal blood vessel oxygen saturation of the retina ($O_{2sat}$) comprising calculating $O_{2sat}$ as follows:

$$O_{2sat} = \frac{\{[OD_{AFV}(\lambda_3) - OD_{AFV}(\lambda_1)]\varepsilon_{Hb}(\lambda_2) - [OD_{AFV}(\lambda_2) - OD_{AFV}(\lambda_1)]\varepsilon_{Hb}(\lambda_3) + [OD_{AFV}(\lambda_2) - OD_{AFV}(\lambda_3)]\varepsilon_{ISO}(\lambda_1)\}}{[OD_{AFV}(\lambda_2) - OD_{AFV}(\lambda_1)]\varepsilon_{HbO-Hb}(\lambda_3) - [OD_{AFV}(\lambda_3) - OD_{AFV}(\lambda_1)]\varepsilon_{HbO-Hb}(\lambda_2)},$$

where $\varepsilon_{HbO-Hb}(\lambda_i) = \varepsilon_{HbO}(\lambda_i) - \varepsilon_{Hb}(\lambda_i)$, and
where $OD_{AFV}$ is optical density of a detected AF signal for a blood vessel of the retina, $\varepsilon_{Hb}$ is a molar extinction coefficient of deoxygenated hemoglobin, $\varepsilon_{HbO}$ is a molar extinction coefficient of oxygenated hemoglobin, and $\varepsilon_{ISO}$ is a molar extinction coefficient at an isosbestic wavelength.

7. The system according to claim 1, the at least one excitation source comprising a first excitation source providing light at a first wavelength ($\lambda_1$) and a second excitation source providing light at a second wavelength ($\lambda_2$) different from $\lambda_1$.

8. The system according to claim 7, the determining of the retinal blood vessel oxygen saturation of the retina ($O_{2sat}$) comprising calculating $O_{2sat}$ as follows:

$$O_{2sat} = \frac{OD_{AFV}(\lambda_2) - OD_{AFV}(\lambda_1)}{\varepsilon_{HbO-Hb}(\lambda_2) \cdot C \cdot d} - \frac{\varepsilon_{Hb}(\lambda_2) - \varepsilon_{ISO}(\lambda_1)}{\varepsilon_{HbO}(\lambda_2) - \varepsilon_{Hb}(\lambda_2)},$$

where $OD_{AFV}$ is optical density of a detected AF signal for a blood vessel of the retina, $\varepsilon_{Hb}$ is a molar extinction coefficient of deoxygenated hemoglobin, $\varepsilon_{HbO}$ is a molar extinction coefficient of oxygenated hemoglobin, C is concentration of hemoglobin in the blood vessel, d is a diameter of the blood vessel, and $\varepsilon_{ISO}$ is a molar extinction coefficient at an isosbestic wavelength.

9. The system according to claim 1, the at least one excitation source comprising a first excitation source providing light at a first wavelength ($\lambda_1$), a second excitation source providing light at a second wavelength ($\lambda_2$) different from $\lambda_1$,
the at least one excitation source comprising a third excitation source providing light at an incident isosbestic wavelength ($\lambda_i$), and
the at least one detector comprising two detectors detecting a portion of the AF light at $\lambda_1$ and $\lambda_2$, one of which is at another isosbestic wavelength.

10. The system according to claim 9, the determining of the retinal blood vessel oxygen saturation of the retina ($O_{2sat}$) comprising calculating $O_{2sat}$ as follows:

$$O_{2sat} = \frac{OD_{AFV}(\lambda_2)(\varepsilon_{ISO} + \varepsilon_{ISOi}) - OD_{ISO}(\lambda_1)(\varepsilon_{Hb} + \varepsilon_{ISOi})}{\varepsilon_{HbO-Hb}(\lambda_2)OD_{ISO}(\lambda_1)},$$

where $OD_{AFV}$ is optical density of a detected AF signal for a blood vessel of the retina, $\varepsilon_{Hb}$ is a molar extinction coefficient of deoxygenated hemoglobin, $\varepsilon_{HbO}$ is a molar extinction coefficient of oxygenated hemoglobin, $\varepsilon_{ISO}$ is an isosbestic molar extinction coefficient at $\lambda_1$, $\varepsilon_{ISOi}$ is an isosbestic molar extinction coefficient at an excitation wavelength, and $OD_{ISO}(\lambda_1) = (\varepsilon_{ISO} + \varepsilon_{ISOi})Cd$, C is concentration of hemoglobin in a blood vessel of the retina, and d is a diameter of the blood vessel of the retina.

11. A method for quantitatively determining retinal blood vessel oxygen saturation, the method comprising:
providing light to a retina using at least one excitation source;
detecting auto-fluorescence (AF) light generated from the retina using at least one detector; and
determining, using a processor, the retinal blood vessel oxygen saturation of the retina based on the AF light detected by the at least one detector.

12. The method according to claim 11, the at least one excitation source being a laser.

13. The method according to claim 11, the at least one excitation source providing light at a wavelength in a range of from 450 nanometers (nm) to 520 nm, and
the light from the at least one excitation source being provided to retinal pigment epithelium (RPE) of the retina.

14. The method according to claim 11, the at least one excitation source comprising a first excitation source providing light at a first wavelength ($\lambda_1$), a second excitation source providing light at a second wavelength ($\lambda_2$) different from $\lambda_1$, and a third excitation source providing light at a third wavelength ($\lambda_3$) different from $\lambda_1$ and $\lambda_2$.

15. The method according to claim 14, the determining of the retinal blood vessel oxygen saturation of the retina ($O_{2sat}$) comprising calculating $O_{2sat}$ as follows:

$$O_{2sat} = \frac{\{[OD_{AFV}(\lambda_3) - OD_{AFV}(\lambda_1)]\varepsilon_{Hb}(\lambda_2) - [OD_{AFV}(\lambda_2) - OD_{AFV}(\lambda_1)]\varepsilon_{Hb}(\lambda_3) + [OD_{AFV}(\lambda_2) - OD_{AFV}(\lambda_3)]\varepsilon_{ISO}(\lambda_1)\}}{[OD_{AFV}(\lambda_2) - OD_{AFV}(\lambda_1)]\varepsilon_{HbO-Hb}(\lambda_3) - [OD_{AFV}(\lambda_3) - OD_{AFV}(\lambda_1)]\varepsilon_{HbO-Hb}(\lambda_2)},$$

where $\varepsilon_{HbO-Hb}(\lambda_i) = \varepsilon_{HbO}(\lambda_i) - \varepsilon_{Hb}(\lambda_i)$, and
where $OD_{AFV}$ is optical density of a detected AF signal for a blood vessel of the retina, $\varepsilon_{Hb}$ is a molar extinction coefficient of deoxygenated hemoglobin, $\varepsilon_{HbO}$ is a molar extinction coefficient of oxygenated hemoglobin, and $\varepsilon_{ISO}$ is a molar extinction coefficient at an isosbestic wavelength.

16. The method according to claim 11, the at least one excitation source comprising a first excitation source providing light at a first wavelength ($\lambda_1$) and a second excitation source providing light at a second wavelength ($\lambda_2$) different from $\lambda_1$.

17. The method according to claim 16, the determining of the retinal blood vessel oxygen saturation of the retina ($O_{2sat}$) comprising calculating $O_{2sat}$ as follows:

$$O_{2sat} = \frac{OD_{AFV}(\lambda_2) - OD_{AFV}(\lambda_1)}{\varepsilon_{HbO-Hb}(\lambda_2) \cdot C \cdot d} - \frac{\varepsilon_{Hb}(\lambda_2) - \varepsilon_{ISO}(\lambda_1)}{\varepsilon_{HbO}(\lambda_2) - \varepsilon_{Hb}(\lambda_2)},$$

where $OD_{AFV}$ is optical density of a detected AF signal for a blood vessel of the retina, $\varepsilon_{Hb}$ is a molar extinction coefficient of deoxygenated hemoglobin, $\varepsilon_{HbO}$ is a molar extinction coefficient of oxygenated hemoglobin, C is concentration of hemoglobin in the blood vessel, d is a diameter of the blood vessel, and $\varepsilon_{ISO}$ is a molar extinction coefficient at an isosbestic wavelength.

18. The method according to claim 11, the at least one excitation source comprising a first excitation source providing light at a first wavelength ($\lambda_1$), and
the at least one detector comprising two detectors.

19. The method according to claim 18, the determining of the retinal blood vessel oxygen saturation of the retina ($O_{2sat}$) comprising calculating $O_{2sat}$ as follows:

$$O_{2sat} = \frac{OD_{AFV}(\lambda_2)(\varepsilon_{iso} + \varepsilon_{isoi}) - OD_{iso}(\lambda_1)(\varepsilon_{Hb} + \varepsilon_{isoi})}{\varepsilon_{HbO-Hb}(\lambda_2)OD_{iso}(\lambda_1)},$$

where $OD_{AFV}$ is optical density of a detected AF signal for a blood vessel of the retina, $\varepsilon_{Hb}$ is a molar extinction coefficient of deoxygenated hemoglobin, $\varepsilon_{HbO}$ is a molar extinction coefficient of oxygenated hemoglobin, $\varepsilon_{ISO}$ is an isosbestic molar extinction coefficient at $\lambda_1$, $\varepsilon_{ISOi}$ is an isosbestic molar extinction coefficient at an excitation wavelength, and $OD_{ISO}(\lambda_1) = (\varepsilon_{ISO} + \varepsilon_{ISOi})Cd$, C is concentration of hemoglobin in a blood vessel of the retina, and d is a diameter of the blood vessel of the retina.

20. A system for quantitatively determining retinal blood vessel oxygen saturation, the system comprising:
   at least one excitation source configured to provide light to a retina;
   at least one detector configured to detect light reflected from the retina; and
   a device in operable communication with the at least one detector and having a processor and a machine-readable medium, the machine-readable medium having instructions stored thereon that, when executed by the processor, determine the retinal blood vessel oxygen saturation of the retina based on auto-fluorescence (AF) of the light detected by the at least one detector,
   the system being configured such that the light from the at least one excitation source is provided to retinal pigment epithelium (RPE) of the retina,
   the at least one excitation source comprising a first laser providing light at a first wavelength ($\lambda_1$), a second laser providing light at a second wavelength ($\lambda_2$) different from $\lambda_1$, and a third laser providing light at a third wavelength ($\lambda_3$) different from $\lambda_1$ and $\lambda_2$,
   at least one of $\lambda_1$, $\lambda_2$, and $\lambda_3$ being in a range of from 450 nanometers (nm) to 520 nm,
   the determining of the retinal blood vessel oxygen saturation of the retina ($O_{2sat}$) comprising calculating $O_{2sat}$ as follows:

$$O_{2sat} = \frac{\{[OD_{AFV}(\lambda_3) - OD_{AFV}(\lambda_1)]\varepsilon_{Hb}(\lambda_2) - [OD_{AFV}(\lambda_2) - OD_{AFV}(\lambda_1)]\varepsilon_{Hb}(\lambda_3) + [OD_{AFV}(\lambda_2) - OD_{AFV}(\lambda_3)]\varepsilon_{ISO}(\lambda_1)\}}{[OD_{AFV}(\lambda_2) - OD_{AFV}(\lambda_1)]\varepsilon_{HbO-Hb}(\lambda_3) - [OD_{AFV}(\lambda_3) - OD_{AFV}(\lambda_1)]\varepsilon_{HbO-Hb}(\lambda_2)},$$

where $\varepsilon_{HbO-Hb}(\lambda_i) = \varepsilon_{HbO}(\lambda_i) - \varepsilon_{Hb}(\lambda_i)$, and where $OD_{AFV}$ is optical density of a detected AF signal for a blood vessel of the retina, $\varepsilon_{Hb}$ is a molar extinction coefficient of deoxygenated hemoglobin, $\varepsilon_{HbO}$ is a molar extinction coefficient of oxygenated hemoglobin, and $\varepsilon_{ISO}$ is a molar extinction coefficient at an isosbestic wavelength.

\* \* \* \* \*